United States Patent [19]

Grill et al.

[11] 4,189,594
[45] Feb. 19, 1980

[54] NOVEL DERIVATIVES OF 1,3-DIPHENOXYPROPANE-2-ON, PROCESS OF THEIR PREPARATION AND THEIR USE AS MEDICAMENTS

[75] Inventors: Helmut Grill, Vaterstetten; Roland Loser, Gauting; Josef Wagner, Grunwald; Rainer H. Zschocke, Munich, all of Fed. Rep. of Germany

[73] Assignee: Klingepharma GmbH & Co., Munich, Fed. Rep. of Germany

[21] Appl. No.: 930,087

[22] Filed: Aug. 1, 1978

[30] Foreign Application Priority Data

Aug. 9, 1977 [DE] Fed. Rep. of Germany ....... 2735856

[51] Int. Cl.² .......................................... CO1B 25/16
[52] U.S. Cl. ..................................... 560/53; 562/463; 424/308; 424/317
[58] Field of Search ......................... 560/53; 562/463; 424/308, 317

[56] References Cited

U.S. PATENT DOCUMENTS

| | | | |
|---|---|---|---|
| 2,792,418 | 5/1957 | Druey et al. | 560/53 |
| 3,378,582 | 4/1968 | Bolhofer et al. | 560/53 |
| 3,948,973 | 4/1976 | Phillips | 560/53 |
| 3,983,164 | 9/1976 | Thorne | 560/53 |

*Primary Examiner*—Paul J. Killos
*Attorney, Agent, or Firm*—Karl W. Flocks

[57] ABSTRACT

Compounds of the formula

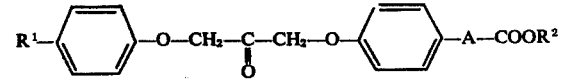

wherein $R^1$ is Cl, Br, $CH(CH_3)_2$ or $C(CH_3)_3$; A is a single bond, $-CH=CH-$ or $-CH_2-CH_2-$; and $R^2$ is H, the cation of a pharmaceutically acceptable salt or an alkyl of up to three carbons, are strong hypolipaemic agents.

5 Claims, No Drawings

NOVEL DERIVATIVES OF 1,3-DIPHENOXYPROPANE-2-ON, PROCESS OF THEIR PREPARATION AND THEIR USE AS MEDICAMENTS

FIELD OF INVENTION

This invention relates to pharmaceuticals and, more particularly, to derivatives of 1,3-diphenoxypropane-on having hypolipaemic activity.

BACKGROUND OF THE INVENTION

The basic substance, 1,3-diphenoxypropane-2-on, was described in 1951 by J. Munch-Petersen (Acta Chem. Scand. 5, 519–528 (1951) and later by M. Baizer (J. Org. Chem. 25, 670–671 (1960). J. Hill (J. Chem. Soc. 1970, 462–464) reported about symmetrically identically substitued compounds, such as 1,3-di-(4'-methylphenoxy)-propane-2-on and 1,3-di-(4'-nitrophenoxy)-propane-2-on. The preparation and use of symmetrically multiply substituted 1,3-diphenoxypropane-2-on compounds can be derived from the U.S. Pat. Nos. 3,655,893 (chloronitrophenyl ethers as nematocides) and 3,666,814 (chloronitrophenyl ethers as herbicides).

Recently, there was a report concerning hypolipaemically effective, symmetrically identically substituted 1,3-diphenoxypropanones, among which the compounds 1,3-di-(4'-methylphenoxy)-propane-2-on and 1,3-di(4'-chlorophenoxy)-propane-2-on should possess the highest activity. (C. Piantadosi, I. H. Hall, S. D. Wyrik and K. S. Ishaq, J. Med. Chem. 19, 222–229 (1976). However, as shown below (Table 3), such compounds do not exhibit a hypolipaemically effect on normally fed, normolipaemic, male Wistar rats weighing 190–230 g.

SUMMARY OF THE INVENTION

Unexpectedly, it has been found that non-symmetrically substituted 1-3-diphenoxypropane-2-ons develop a strong hypolipaemic effect when one of the substituents is a carboxyl group, and this is so even though the compound is in the form of salt or even in esterified form.

DETAILED DESCRIPTION OF EMBODIMENTS

Compounds of the general formula (2)

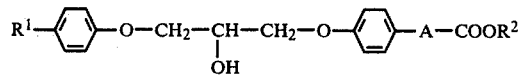

wherein
$R^1$ is —Cl, —Br, $CH(CH_3)_2$, or —$C(CH_3)_3$;
A is a single bond, —CH=CH—, or —$CH_2$—$CH_2$—;
$R^2$ is hydrogen, the cation of a pharmaceutically acceptable salt or a straight or branched, saturated or unsaturated alkyl radical comprising up to three atoms, which may have a methoxy group in the end position, can be converted with various agents into the corresponding ketones.

For example, the oxidation can be performed in acetonic medium with aqueous, sulfuric-acid chromium trioxide solutions (Jones reagent). The oxidation takes place with a good yield also in anhydrous, inert organic solvents, such as ether with dimethylsulfoxide, dicyclohexylcarbodiimide and trifluoroacetic acid in connection with addition of pyridine. One can also use mixtures of dimethylsulfoxide and trifluoroacetic acid anhydride in halogenated hydrocarbons, such as methylene chloride. For a controlled oxidation it is of essential importance to maintain certain criteria of reaction, as described more in detail in the examples.

Compounds of the general formula (1)

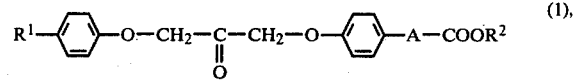

wherein $R^1$ and A possess the significance indicated above and $R^2$ represents a hydrogen atom, can be obtained also from compounds of the general formula (2), wherein $R^1$ and A possess the above-mentioned significance and $R^2$ represents an alkyl group, preferably a methyl group, or can even be a benzyl group. The compounds are here first converted into the corresponding ketones and then subjected to cautious alkaline saponification or, in the case of the benzyl ester, with particular advantage hydrogenolytically split to the acid.

Compounds of the general formula (2) can be easily prepared in accordance with processes as already described in the DOS No. 24 60 689. Compounds of the general formula (3)

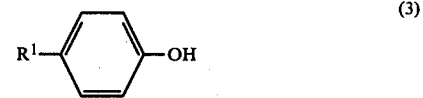

wherein $R^1$ represents an atom of chlorine or bromine or an isopropyl or tertiary butyl group, can thus be reacted with a glycidylether of the general formula (4)

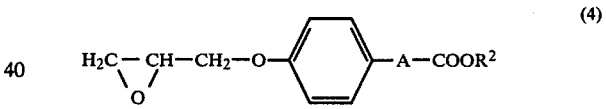

wherein A indicates a single bond, a vinylene or ethylene group and $R^2$ represents a straight or branched, saturated or unsaturated alkyl radical having 1-3 carbon atoms, which possibly carries a methoxy group in the end position, in organic-protic solvents, preferably alcohols, that correspond to the alkyl radical, in the presence of bases, with advantageous alkali hydroxides or Lewis acids, e.g., borotrifluoridetherate.

Also compounds of the general formula (5)

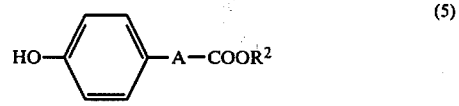

wherein A and $R^2$ possess the significance indicated in the general formula (4), can likewise be reacted in the same manner with a glycidylether of the general formula (6)

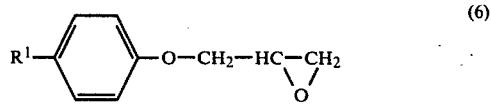

wherein $R^1$ possesses the significance indicated in the general formula (3).

The compounds of the general formula (1) and their salts are preferably administered orally. The oral daily dosage for adults ordinarily amounts to 0.1–10 g, preferably 0.5–3 g. A unit dosage form suitably comprises 10–500 mg. of active compound.

The effective substances can be confectioned in ordinary forms for oral administration using conventional diluents and carriers, e.g., as capsules, liquids, tablets or powders. They can be processed into dragee cores or tablets by mixing with solid, pulverulent substances, such as lactose, sucrose, sorbite, mannite, potato starch or cornstarch, cellulose derivatives or gelatin, possibly by adding lubricants, such as magnesium or calcium stearate or polyethylene glycols.

As further forms of administration, one can use insertion-type capsules, e.g., of hard gelatin, as well as closed soft-gelatin capsules comprising a softener, e.g., glycerin. The insertion-type capsules contain the effective substance preferably in the form of granulate, e.g., in mixture with fillers, such as lactose, sucrose, mannite, starches, e.g., potato starch, cornstarch or amylopectin, cellulose derivatives gelatine or highly dispersed silicic acids. Soft capsules contain the effective substance preferably dissolved or suspended in suitable liquids, e.g., in vegetable oil or polyethylene glycols.

The invention is explained more in detail below by means of the following exemplified embodiments.

EXAMPLE 1

3-(4'-methoxycarbonylphenoxy)-(4'-chlorophenoxy)-propane-2-on (a) Preparation of starting material 3-(4'-methoxycarbonylphenoxy)-1-(4'-chlorophenoxy)-propane-2-ol To the solution of 2.24 g (0.04 mol) potassium hydroxide in 300 ml absolute methanol, there is added 36.60 g (0.24 mol) 4'-hydroxybenzoic-acid methylester and the mixture is slowly heated to boiling. In the course of one hour, there is added 36.92 g (0.2 mol) 3-(4'-chlorophenoxy)-1,2-epoxypropane to the mixture, which is heated for 21 hours under reflux. The solvent is then removed in vacuo, the residue is dissolved in ether and washed with water to neutral reaction. The organic phase is dried over sodium sulfate and concentrated. About 50 g crude product is obtained which is recrystallized from carbon tetrachloride.

Colorless crystals, melting point 88°–90°; yield 60.0%.

$C_{17}H_{17}ClO_5$ (336.78): Calculated: C, 60.63; H, 5.09. Found: C, 60.89; H, 5.29.

IR-spectrum (KBr)[1]: $\nu$(OH): 3500 cm$^{-1}$; $\nu$(C=O):1685 cm$^{-1}$.

$^1$H-NMR-spectrum (CDCl$_3$)[2]: 2.7 d (1) OH, 3.8 s (3) COOCH$_3$, 4.2 m (4) CH$_2$, 4.3 m (1) CHOH, 6.7–8.1 m (8) aromate.

[1]The IR-spectra were recorded with an apparatus of Perkin-Elmer, Type 257.
[2]The $^1$H-NMR-spectra were recorded with the Varian-Spectrometer EM-360, the chemical shifts are indicated in ppm against TMS (=0.0), the relative intensities are added within brackets. s=singlet, d—doublet, t—triplet, m—multiplet (b) Preparation of 3-(4'-methoxycarbonylphenoxy)-1-(4'-chlorophenoxy)-propane-2-on in accordance with the invention by means of oxidation with chromic acid The solution of 33.67 g (0.1 mol) 3-(4'-methoxycarbonylphenoxy)-1-(4'-chlorophenoxy)-propane-2-ol in 350 ml acetone (distilled over potassium permanganate), while subjected to ice cooling, is mixed with 100 ml Jones reagent (prepared from 40 g chromium trioxide, 20 ml concentrated sulfuric acid and 80 ml water), so that the temperature of the reaction does not rise above +10° C. The mixture is then stirred at room temperature until no initial compound can be determined in the thin-layer chromatogram. After mixing with the double amount of water, extraction with chloroform is repeatedly carried out. The organic phase is first washed with a solution of sodium bicarbonate and then with water. Finally, it is dried over magnesium sulfate and concentrated in vacuo. Colorless crystals, melting point 100° C. (acetic ester/petrol ether): yield 24.45 g (73.0%).

$C_{17}H_{15}ClO_5$ (334.76): Calculated: C, 60.99; H, 4.52. Found: C, 60.88; H, 4.70.

Molecular weight: 334 (determined through mass spectrometry)[1]

IR-spectrum (KBr): $\nu$(C=O): 1740 cm$^{-1}$ (ketone), 1700 cm$^{-1}$ (ester) no absorption in the $\nu$(OH) range.

$^1$H-NMR-spectrum (CCl$_4$): 3.8 s (3) COOCH$_3$, 5.0 s (2) OCH$_2$, 5.1 s (2) OCH$_2$. 6.8–8.1 m (8) aromate.
[1]The mass spectra were recorded with the mass spectrometer Varian MAT 112 S by means of electron-impact ionization.

(c) Preparation of 3-(4'-methoxycarbonylphenoxy)-1-(4'-chlorophenoxy)-propane-2-on in accordance with the invention, by means of DMSO-oxidation With exclusion of moisture, a solution of 33.67 g (0.1 mol) 3-(4'-methoxycarbonylphenoxy)-1-(4'-chlorophenoxy)-propane-2-ol in 500 ml absolute ether is mixed at room temperature with 40 ml dimethylsulfoxide, 7 ml pyridine and 30.95 g (0.15 mol) dicyclohexylcarbodiimide. On adding 5 ml trifluoroacetic acid by drops, the reaction sets in, as manifested by the appearance of a colorless precipitate. After four hours of stirring at room temperature, the reaction is completed according to the thin-layer chromatogram. In order to eliminate excessive dicylcohexylcarbodiimide, the reaction mixture is mixed in portions with a solution of 30 g oxalic acid in methanol and stirred for 20 minutes. After the precipitate is separated, the filtrate is washed with a solution of sodium hydrocarbonate and then with water. The organic phase is dried over sodium sulfate and concentrated in vacuo.

Colorless crystals, melting point 100° C. (acetic ester/petrol ether): yield 26.80 (80.1%). The IR, $^1$H-NMR and mass spectra are identical with the substance prepared in accordance with example 1b.

EXAMPLE 2

3-(4'-[2-(2-propinoxycarbonyl)-ethyl]-phenoxy)-1-(4'-bromophenoxy)-propane-2-on

A solution is prepared from 43.35 g (0.1 mol) 3-[2-(2-propinoxycarbonyl)-ethyl]-phenoxy)-1-(4'-bromophenoxy)-propane-2-ol in 500 ml absolute ether and mixed at room temperature with 40 mol dimethylsulfoxide, 7 ml pyridine and 30.95 g (0.15 mol) dicyclohexylcarbodiimide. After adding 5 ml trifluoroacetic acid, the mixture is stirred until no starting compound can be determined through thin-layer chromatographic control. In order to eliminate excessive dicyclohexylcarbodiimide, the reaction mixture is mixed in portions with a solution of 30 g oxalic acid in methanol and stirred for 20 minutes. After the dicyclohexyl-urea precipitate formed is separated, the filtrate is washed with a solution of sodium hydrocarbonate and then with water. The organic phase is dried over sodium sulfate and concentrated in vacuo. The raw product is recrystallized twice. Colorless crystals, melting point 90°–1° C. (isopropanol): yield 37.56 g (87.1%).

$C_{21}H_{19}BrO_5$ (431.27): Calculated: C, 58.48; H, 4.44. Found: C, 58.38; H, 4.45.

Molecular weight: 431 (determined through mass spectrometry)

IR-spectrum (KBr): $\nu(\equiv CH)$: 3280 cm$^{-1}$, $\nu(C=O)$: 1740 cm$^{-1}$ (ketone), 1730 cm$^{-1}$ (ester). No absorption in the $\nu(OH)$ range.

$^1$H-NMR-spectrum (CDCl$_3$): 2.4 t (1) $\equiv$CH, 2.5–3.1 m (4) C$\underline{H_2}$C$\underline{H_2}$, 4.2 d (2) C$\underline{H_2}$C$\equiv$, 4.7 s (2) OC$\underline{H_2}$, 4.8 s (2) OC$\underline{H_2}$, 6.6–7.5 m (8) aromate.

Further carboxylic-acid esters of the general formula (1) were prepared in analogy to the Examples 1 and 2. Such esters are listed with their physical characteristics in the following table. For the sake of completeness, the compounds described in the examples are indicated once more in the following tables.

Table 1

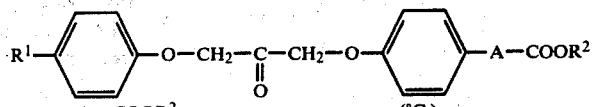

(1)

| No. | R$^1$ | A—COOR$^2$ | mp (°C.) | |
|---|---|---|---|---|
| 1 | Cl | COOCH$_3$ | 100 | (acetic ester/ petrol ether) |
| 2 | Cl | COOCH$_2$CH$_2$CH$_3$ | 90–1 | (Isopropanol) |
| 3 | Cl | COOCH$_2$CH=CH$_2$ | 66–8 | (Isopropanol) |
| 4 | Cl | COOCH$_2$C≡CH | 83 | (Isopropanol) |
| 5 | Cl | COOCH$_2$OCH$_3$ | 95–6 | (Isopropanol) |
| 6 | Cl | COOCH$_2$CH$_2$OCH$_3$ | 93 | (Isopropanol) |
| 7 | Cl | CH=CHCOOCH$_3$ | 117–8 | (Methanol) |
| 8 | Cl | CH=CHCOOCH$_2$CH$_2$CH$_3$ | 95–7 | (carbon tetrachloride) |
| 9 | Cl | CH=CHCOOCH$_2$CH$_2$OCH$_3$ | 79–80 | (carbon tetrachloride) |
| 10 | Cl | CH$_2$CH$_2$COOCH$_3$ | 81–2 | (acetic ester/petrol ether) |
| 11 | Cl | CH$_2$CH$_2$COOCH$_2$CH$_2$CH$_3$ | 75–6 | (Isopropanol) |
| 12 | Cl | CH$_2$CH$_2$COOCH$_2$CH=CH$_2$ | 68–9 | (Methylcyclohexane) |
| 13 | Cl | CH$_2$CH$_2$COOCH$_2$OCH$_3$ | 89–90 | (Isopropanol) |
| 14 | Cl | CH$_2$CH$_2$COOCH$_2$CH$_2$OCH$_3$ | x* | $n_D^{20} = 1.546$ |
| 15 | Br | COOCH$_3$ | 113–4 | (Isopropanol) |
| 16 | Br | COOCH$_2$CH$_2$CH$_3$ | 98–9 | (Isopropanol) |
| 17 | Br | COOCH$_2$CH=CH$_2$ | 84–5 | (Isopropanol) |
| 18 | Br | COOCH$_2$CH$_2$OCH$_3$ | 99–100 | (Isopropanol) |
| 19 | Br | CH=CHCOOCH(CH$_3$)$_2$ | 103–4 | (Isopropanol) |
| 20 | Br | CH=CHCOOCH$_2$C≡CH | 103–4 | (Isopropanol) |
| 21 | Br | CH=CHCOOCH$_2$CH$_2$OCH$_3$ | 83–4 | (Isopropanol) |
| 22 | Br | CH$_2$CH$_2$COOCH$_2$CH=CH$_2$ | 67–8 | (Isopropanol) |
| 23 | Br | CH$_2$CH$_2$COOCH$_2$C≡CH | 90–1 | (Isopropanol) |
| 24 | (CH$_3$)$_2$CH | COOCH$_3$ | 77–8 | (carbon tetrachloride) |
| 25 | (CH$_3$)$_2$CH | COOCH$_2$CH$_3$ | 71–2 | (methanol/water) |
| 26 | (CH$_3$)$_2$CH | COOCH(CH$_3$)$_2$ | 63–4 | (petrol ether) |
| 27 | (CH$_3$)$_2$CH | COOCH$_2$CH=CH$_2$ | 69–70 | (Methylcyclohexane) |
| 28 | (CH$_3$)$_2$CH | CH=CHCOOCH$_3$ | 90–1 | (acetone/petrol ether) |
| 29 | (CH$_3$)$_2$CH | CH=CHCOOCH$_2$CH$_2$OCH$_3$ | 79 | (Isopropanol) |
| 30 | (CH$_3$)$_3$C | COOCH$_3$ | 106 | (acetone/petrol ether) |
| 31 | (CH$_3$)$_3$C | COOCH$_2$CH$_3$ | 69–70 | (Isopropanol) |
| 32 | (CH$_3$)$_3$C | COOCH(CH$_3$)$_2$ | 82–3 | (Diisopropyl ether) |
| 33 | (CH$_3$)$_3$C | COOCH$_2$CH=CH$_2$ | 58 | (acetone/petrol ether) |
| 34 | (CH$_3$)$_3$C | COOCH$_2$C≡CH | 118–20 | (Isopropanol) |
| 35 | (CH$_3$)$_3$C | COOCH$_2$OCH$_3$ | 64–5 | (chloroform/petrol ether) |
| 36 | (CH$_3$)$_3$C | COOCH$_2$CH$_2$OCH$_3$ | 59–60 | (Isopropanol) |
| 37 | (CH$_3$)$_3$C | CH=CHCOOCH$_3$ | 98–9 | (Isopropanol) |
| 38 | (CH$_3$)$_3$C | CH=CHCOOCH$_2$CH$_2$OCH$_2$ | 70–1 | (chloroform/ petrol ether) |
| 39 | (CH$_3$)$_3$C | CH$_2$CH$_2$COOCH$_3$ | 66–7 | (Isopropanol) |
| 40 | (CH$_3$)$_3$C | CH$_2$CH$_2$COOCH(CH$_3$)$_2$ | x* | $n_D^{20} = 1.527$ |
| 41 | (CH$_3$)$_3$C | CH$_2$COOCH$_2$CH=CH$_2$ | x* | $n_D^{20} = 1.536$ | x*Oil purified through column chromatography.

EXAMPLE 3

3-(4'-carboxyphenoxy)-1-(4'-tert.butylphenoxy)-propane-2-on (a) preparation by means of oxidation with chromic acid A solution is prepared from 34.44 g (0.1 mol) 3-(4'-carboxyphenoxy)-1-(4'-tert.butylphenoxy)-propane-2-ol in 500 ml acetone (distilled over potassium permanganate) and, while the solution is cooled by ice, there is added by drops 110 ml Jones reagent (for the preparation see example 1b) in such a manner that the temperature of the reaction does not rise above +10° C. The material is then stirred for further eight hours at room temperature, whereafter it is processed as in example 1b. Colorless crystals, melting point 164° C. (acetone): yield 11.8 g (34.4%).

$C_{20}H_{22}O_5$ (342.39) calculated: C, 70.16; H, 6.48. Found: C, 70.30; H, 6.42.

Molecular weight: 342 (determined through mass spectrometry)

IR-spectrum (KBr): $\nu(C=O)$: 1740 cm$^{-1}$ (ketone), 1670 cm$^{-1}$ (carboxylic acid), no absorption in the $\nu(OH)$ range.

$^1$H-NMR-spectrum (d$_6$-DMSO/d$_6$-acetone): 0.9 s (9) (C$\underline{H}_3$)$_3$C, 4.6 s (2) OC$\underline{H}_2$, 4.8 s (2) OC$\underline{H}_2$, 6.4–7.8 m (9) COO$\underline{H}$, aromate.

(b) Preparation by means of DMSO oxidation

Into the solution of 14.2 ml (0.2 mol) anhydrous dimethylsulfoxide in 150 ml methylene chloride, there is added by drops 20.9 ml (0.15 mol) of trifluoroacetic acid enhydride in 35 ml methylene chloride at −70° C. and the material is stirred for about ten minutes until a colorless precipitate appears. Then there is added a solution of 34.44 g (0.1 mol) 3-(4′-carboxyphenoxy)-1-(4′-tert. butylphenoxy)-propane-2-ol in 70 ml methylene chloride as well as 13.5 ml dimethylsulfoxide in such a manner that the temperature in the reactive mixture does not rise above −60° C. After thirty minutes, there is cautiously added 40 ml triethyl amine and, after the cold bath is removed, the reactive mixture is brought to room temperature. Through an addition of water, the oxidation product in the form of a colorless precipitate is obtained, which can be recrystallized from acetone. Colorless crystals, melting point 164° C. (acetone): yield 14.8 g (43.3%). The IR, $^1$H-NMR and mass spectra are identical with the product prepared in accordance with the example 3a.

EXAMPLE 4

3-[4′-(2-carboxyvinyl)-phenoxy)]-1-(4′-chlorophenoxy)-propane-2-on

To a solution of 36.08 g (0.1 mol) 3-[4′-(2-methoxycarbonyl-vinyl)-phenoxy]-1-(4′-chlorophenoxy)-propane-2-on in 1000 ml methanol, there is added by drops 200 ml aqueous 2 n solution of potassium hydroxide, while the solution is stirred, and the reactive mixture is left standing at room temperature until no starting compound can be determined through thin-layer chromatography. The mixture is then concentrated in vacuo, the residue is absorbed in water and cautiously mixed with 0.5 n sulfuric acid until a weak acid reaction is obtained. After washing with water, the precipitated acid is dried over phosphorous pentoxide in vacuo and then recrystallized. Colorless crystals, melting point 173°–5° C. (acetone): yield 10.0 g (28.9%).

C$_{18}$H$_{15}$ClO$_5$ (346.8): Calculated: C, 62.34; H, 4.36. Found: C, 62.07; H, 4.41.

Molecular weight: 346 (determined through mass spectrometry)

IR-spectrum (KBr): ν(C═O): 1730 cm$^{-1}$ (ketone), 1760 cm$^{-1}$ (carboxylic acid), ν(C═C): 1630 cm$^{-1}$, no absorption in the ν(OH) range.

$^1$H-NMR spectrum (d$_6$-DMSO) 5.0 s (4) OC$\underline{H}_2$, 6.3 d (1) (C$\underline{H}$COOH, 7.5 d (1) C$\underline{H}$C$_6$H$_4$, 6.8–7.6 m (8) aromate, 12.1 s (1) COO$\underline{H}$.

EXAMPLE 5

3-[4′-(2-carboxyethyl)-phenoxy]-1-(4′-chlorophenoxy)-propane-2-on

A solution of 44.0 g (0.1 mol) 3-[4′-(2-phenylmethoxycarbonylethyl)-phenoxy]-1-(4′-chlorophenoxy)-propane-2-on in 1000 ml acetone is mixed with 1 ml acetic acid and, after the addition of 8 g (10%) palladium/carbon, hydrogenated until the calculated amount of hydrogen is absorbed. After the catalyst is separated, the filtrate is concentrated in vacuo, the residue is absorbed in chloroform and the acid is precipitated through addition of petrol ether. Colorless crystals, melting point 114°–5° C. (trichloroethylene): yield 24.20 g (69.4%).

C$_{18}$H$_{17}$ClO$_5$ (348.77): Calculated: C, 61.99; H, 4.91. Found: C, 61.93; H, 4.99.

Molecular weight: 348 (determined through mass spectrometry)

IR-spectrum (KBr): ν(C═O): 1730 cm$^{-1}$ (ketone) 1700 cm$^{-1}$ (carboxylic acid), no absorption in the ν(OH) range $^1$H-NMR-spectrum (d$_6$-acetone): 2.3–3.1 m (4) C$\underline{H}_2$C$\underline{H}_2$, 4.9 s (2) OC$\underline{H}_2$, 5.0 s (2) OC$\underline{H}_2$, 6.7–7.4 m (9) COO$\underline{H}$, aromate.

While using the processes indicated in Examples 3–5, further carboxylic acids in accordance with formula (1) were prepared and listed in Table 2.

Table 2

$$R^1-\bigcirc-O-CH_2-\underset{\underset{O}{\|}}{C}-CH_2-O-\bigcirc-A-COOR \quad (1)$$

| No. | R$^1$ | A—COOR$^2$ | mp (°C.) |
|---|---|---|---|
| 42 | Cl | COOH | 180–1 (acetone) |
| 43 | Cl | CH═CHCOOH | 173–5 (acetone) |
| 44 | Cl | CH$_2$CH$_2$COOH | 114–5 (trichloroethylene) |
| 45 | Br | COOH | 189–90 (acetic ester) |
| 46 | Br | CH═CHCOOH | 183–4 (acetone) |
| 47 | Br | CH$_2$CH$_2$COOH | 124–5 (benzene) |
| 48 | (CH$_3$)$_2$CH | COOH | 158–9 (chloroform) |
| 49 | (CH$_3$)$_2$CH | CH═CHCOOH | 170–1 (acetone) |
| 50 | (CH$_3$)$_3$C | COOH | 164 (acetone) |
| 51 | (CH$_3$)$_3$C | CH═CHCOOH | 177–8 (trichloroethylene) |
| 52 | (CH$_3$)$_3$C | CH$_2$CH$_2$COOH | 102–3 (chloroform/petrolether) |

EXAMPLE 6

Medicament containing 3-[4′-(2-isopropoxycarbonylethyl)-phenoxy]-1-(4′-tert.butylphenoxy)-propane-2-on A mixture is prepared from 250 g 3-[4′-(2-isopropoxycarbonylethyl)-phenoxy]-1-(4′-tert.-butylphenoxy)-propane-2-on and 250 g polyethylene glycol and filled into 1000 soft-gelatin capsules in accordance with the Scherer method, the capsules containing 250 mg effective substance in each case.

EXAMPLE 7

Medicament containing 3-(4′-methoxymethoxycarbonylphenoxy)-1-(4′-chlorophenoxy)-propane-2-on A mixture is produced by effectively mixing 100 g 3-(4′-methoxymethoxycarbonylphenoxy)-1-(4′-chlorophenoxy)-propane-2-on, 16 g cornstarch and 6 g highly-dispersed silicon dioxide, which is then moistened with a solution of 2 g stearic acid, 6 g acetyl cellulose and 6 g stearic in 70 ml isopropanol, the moistening being followed by granulation. The dried granulate is sieved and, after mixing with 16 g cornstarch, 16 g talc and 2 g magnesium stearate, it is pressed into 1000 dragée cores. After such cores are coated with a syrup of 2 g lacca, 7.5 g gum arabic, 0.15 g dye, 2 g colloidal silicon dioxide, 25 g talc and 53.35 g sucrose and the coated cores are dried, 1000 dragées are obtained, each weighing 260 mg and containing 100 mg effective substance.

EXAMPLE 8

Medicament containing 3-(4'-carboxyphenoxy)-1-(4'-tert.butylphenoxy)-propane-2-on A finely pulverized mixture of 250 g 3-(4'-carboxyphenoxy)-1-(4'-tert.butylphenoxy)-propane-2-on, 133 g cornstarch, 12 g magnesium stearate and 5 g gelatin is passed through a fine-mesh screen and then filled dry into 1000 hard gelatin capsules, containing 250 mg effective substance in each case.

EXAMPLE 9

Pharmacological Testing

(1) Oral Tolerance

Oral acute toxicity was determined by the oral application of the test compounds to mice, NMR-I strain, weight 15–20 g. The $LD_{50}$-values were calculated in accordance with Litchfield-Wilcoxon (J. Pharmacol. Ex. Ther. 96, 99 (1949)) and relate to the eighth day of the treatment. The $LD_{50}$-values for CLOFIBRAT, i.e., 2-(4'-chlorophenoxy)-2-methylpropionic-acid-ethylester, amounted to about 1900 mg/kg in this test series. The tested substances of the invention were throughout better tolerated and superior than the CLOFIBRAT.

(2) Lipid-lowering Effect

The lipid-lowering effect was tested on groups containing in each case 10 normally fed ("ssniff" combination feed) normolipaemic male Wistar (Ivanovas-Kisslegg) rats, weighing 190–230 g. The test compounds were absorbed in an aqueous solution of 0.25% agar and 0.85% NaCl and administered orally. After the application of 4×100 mg/kg through a period of three days, the animals were left without feed for four hours and bled through heart puncture (R. Zschocke, H. Enomoto, R. Löser and G. Hofrichter, Proc. 25, Coll. Protides Biol. Fluids, Editor H. Peeters). The serum lipids were determined with a Technicon Autoanalyzer. The total cholesterol (TC) was determined with the enzymatic color test (R. Roschlau et al, U. Klin. Chem. u. Klin. Biochem, 12, 403, (1974)). The quantitative analysis of the triglycerides (TG) was effected in accordance with Eggstein and Kreutz (Klin. Wschr. 44, 262 (1966)), modified for the Autoanalyzer.

The lipid-lowering effect is expressed as the percentage-wise lowering of the total cholesterol and the triglycerides in relation to the control. Every tested compound of the invention was superior to the CLOFIBRAT in at least one value.

Table 3

Lowering of the level of triglyceride (TG) and total cholesterol (TC) in rat serum after oral administration of the test substances, expressed in percentage.

| Comparative tests with compounds of the prior art | Lowering in % | |
|---|---|---|
| | TG $X \pm S_x$ | TC $X \pm S_x$ |
| CLOFIBRAT | 48.1 ± 10.6 | 26.3 ± 6.4 |
| 1,3-di-(4-methylphenoxy)-propane-2-on* | −27.9 ± 16.0 | −2.3 ± 14.5 |
| 1,3-di-(4'-chlorophenoxy)-propane-2-on* | −30.6 ± 50.1 | −6.3 ± 10.8 |

| Compounds of the invention listed in Tables 1 and 2 Compound No. | | |
|---|---|---|
| 1 | 72.1 ± 4.3 | 25.9 ± 16.1 |
| 2 | 69.7 ± 10.8 | 29.5 ± 7.6 |
| 3 | 74.9 ± 8.9 | 33.4 ± 18.6 |
| 4 | 83.1 ± 4.7 | 39.9 ± 14.2 |
| 5 | 73.8 ± 19.3 | 38.2 ± 11.7 |
| 6 | 77.8 ± 8.0 | 39.3 ± 12.5 |
| 7 | 86.3 ± 11.2 | 26.9 ± 19.7 |
| 9 | 62.6 ± 8.3 | 37.3 ± 11.1 |
| 10 | 79.5 ± 8.6 | 20.1 ± 20.9 |
| 11 | 68.3 ± 8.5 | 24.3 ± 18.8 |
| 12 | 82.6 ± 8.3 | 39.1 ± 11.4 |
| 13 | 66.0 ± 7.4 | 25.7 ± 12.4 |
| 14 | 81.0 ± 8.3 | 36.0 ± 7.6 |
| 15 | 69.0 ± 14.2 | 30.1 ± 16.8 |
| 16 | 87.3 ± 10.2 | 36.2 ± 10.6 |
| 17 | 76.9 ± 7.4 | 28.6 ± 10.6 |
| 22 | 76.8 ± 8.5 | 30.8 ± 11.9 |
| 23 | 55.9 ± 9.1 | 26.7 ± 12.2 |
| 24 | 61.2 ± 6.8 | 22.7 ± 11.9 |
| 25 | 65.0 ± 6.9 | 14.2 ± 10.8 |
| 30 | 70.9 ± 5.4 | 28.5 ± 12.2 |
| 31 | 59.0 ± 12.3 | 19.0 ± 12.4 |
| 32 | 74.2 ± 6.7 | 17.6 ± 9.7 |
| 33 | 69.4 ± 7.4 | 30.5 ± 9.2 |
| 35 | 88.2 ± 5.6 | 22.9 ± 7.9 |
| 36 | 69.5 ± 18.8 | 30.4 ± 11.4 |
| 40 | 81.6 ± 8.9 | 37.5 ± 7.3 |
| 41 | 92.7 ± 4.1 | 39.3 ± 9.5 |
| 42 | 68.4 ± 7.9 | 25.3 ± 15.9 |
| 43 | 67.7 ± 11.3 | 24.6 ± 14.5 |
| 44 | 84.9 ± 9.2 | 42.0 ± 8.8 |
| 45 | 72.5 ± 5.0 | 23.1 ± 11.3 |
| 46 | 64.7 ± 10.4 | 24.6 ± 12.8 |
| 48 | 77.8 ± 4.8 | 20.2 ± 11.1 |
| 49 | 88.6 ± 12.0 | 21.6 ± 11.0 |
| 50 | 76.3 ± 5.7 | 39.9 ± 11.1 |
| 51 | 84.0 ± 4.6 | 24.1 ± 13.6 |
| 52 | 88.5 ± 8.3 | 43.2 ± 9.9 |

*C. Piantadosi et al., J. Med. Chem. 19, 222 (1976)

It will be obvious to those skilled in the art that various changes may be made without departing from the scope of the invention and the invention is not to be considered limited to what is described in the specification.

What is claimed is:

1. A derivative of 1,3-diphenoxypropane-2-on having the formula (1)

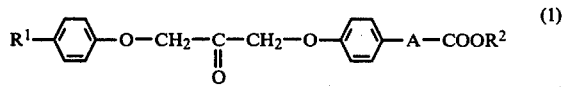

(1)

or a pharmaceutically acceptable salt thereof, wherein
$R^1$ is —Cl, —Br, CH(CH$_3$)$_2$, or —C(CH$_3$)$_3$;
A is a single bond, —CH=CH—, or —CH$_2$—CH$_2$—;
$R^2$ is hydrogen, the cation of a pharmaceutically acceptable salt or a straight or branched, saturated or unsaturated alkyl radical comprising up to three carbon atoms, which may have a methoxy group in the end position.

2. A medicament consisting essentially of an hypolipaemically-effective amount of a compound in accordance with claim 1, and a pharmaceutically acceptable diluent or carrier.

3. A medicament as in claim 2, in a single dosage unit and containing 10–500 mg of said compound.

4. A method of lowering the lipid content of the blood in a patient in need of said therapy comprising administering to said patient an hypolipaemically-effective amount of a compound in accordance with claim 1.

5. A method in accordance with claim 4 wherein said hypolipaemically-effective amount is 0.5 to 3 g. per day administered orally.

* * * * *